United States Patent [19]

Keys

[11] Patent Number: 5,039,302
[45] Date of Patent: Aug. 13, 1991

[54] DENTAL BRACKET INSTRUMENT

[75] Inventor: Mark D. Keys, San Diego, Calif.

[73] Assignee: Johnson & Johnson Consumer Products, Inc., New Brunswick, N.J.

[21] Appl. No.: 473,810

[22] Filed: Feb. 1, 1990

[51] Int. Cl.⁵ ............................................. A61C 7/00
[52] U.S. Cl. ...................................... 433/3; 433/141
[58] Field of Search ................ 433/3, 8, 10, 11, 13, 433/16, 17, 141

[56] References Cited

U.S. PATENT DOCUMENTS

| | | | |
|---|---|---|---|
| 1,261,339 | 4/1918 | Angle | 433/3 |
| 2,835,972 | 5/1958 | Sheldon | 433/3 |
| 3,686,762 | 8/1972 | Sutter | 433/3 |
| 4,103,423 | 8/1978 | Kessel | 433/10 |
| 4,127,940 | 12/1978 | Shilliday | 433/3 |
| 4,419,078 | 12/1983 | Pletcher | 433/10 |
| 4,465,461 | 8/1984 | Schütz | 433/3 |
| 4,559,012 | 12/1985 | Pletcher | 433/10 |
| 4,655,708 | 4/1987 | Fujita | 433/10 |
| 4,712,999 | 12/1987 | Rosenberg | 433/8 |

FOREIGN PATENT DOCUMENTS 1146031  3/1985  U.S.S.R. ................ 433/3

Primary Examiner—Gene Mancene
Assistant Examiner—Michael Lynch
Attorney, Agent, or Firm—Paul A. Coletti

[57] ABSTRACT

An instrument for opening and closing a dental bracket where the bracket has a cover for an archwire slot. The instrument contains projections rotating about the archwire, a key fitting behind the cover and causes the cover to telescope into the bracket.

4 Claims, 3 Drawing Sheets

DENTAL BRACKET INSTRUMENT

FIELD OF THE INVENTION

The present invention relates generally to instruments for use with dental brackets. More specifically, the invention relates to an instrument for use in opening and closing a dental bracket having a hinged clip archwire slot cover.

BACKGROUND OF THE INVENTION

Currently, there are in use many various forms of dental brackets. One of the more popular forms are dental brackets which have archwire slots which may be covered. In some of these brackets, the archwire slot is protected by a rotatable cover. In other words, the cover is placed over the archwire after the archwire has been emplaced in the archwire slot.

As is well known, these brackets are extremely small, and can be very tedious in handling. As can be imagined, it is even more tedius to place and close an archwire slot cover over a dental bracket after having placed an archwire strand in the bracket. In some instances, an orthodontist can use tweezers to rotate the cover over the archwire. However, in some hard to reach places it may be awkward, difficult, or even impossible to hinge the cover over the archwire slot. In these instances extreme dexterity is necessary in order to overcome the tight tolerances within the mouth.

SUMMARY OF THE INVENTION

It is an object of the present invention to provide an instrument for closure of an archwire slot cover on a dental bracket.

It is another object of the invention to provide an instrument which allow the orthodontist to open and close the dental bracket in tight spaces within the mouth, after emplacement of the bracket on the tooth.

It is yet another object of the invention to provide a dental bracket instrument which allows the user to open and close dental brackets after emplacement on the tooth, so that archwire can be removed and replaced easily.

These and other objects of the invention are accomplished in a dental bracket instrument which comprises a long tube having a double right angled projection at its end. This projection may be tapered to a point so that the point fits easily under the closed hinge cover of the dental bracket, and rotates around the archwire. In this way, the right angled projection allows the tapered point to be placed abutting the hinge cover, and can be used to either open or close the cover.

This arrangement works more readily than tweezers where either the tweezers must be placed at right angles to the hinged cover, or, if placed parallel to the cover must be manipulated so that the user's hand is parallel to the cover. Often, this will result in the inability to reach certain inconvenient areas within the mouth. With the instrument of the invention, because the hand is free and spaced away from the dental bracket, opening and closing the cover is quite simple.

The foregoing invention will be better understood in connection with the attached Detailed Description of the Drawings taken in conjunction with the following Detailed Description of the Invention.

DETAILED DESCRIPTION OF THE DRAWINGS

DETAILED DESCRIPTION OF THE INVENTION

Figure 1:
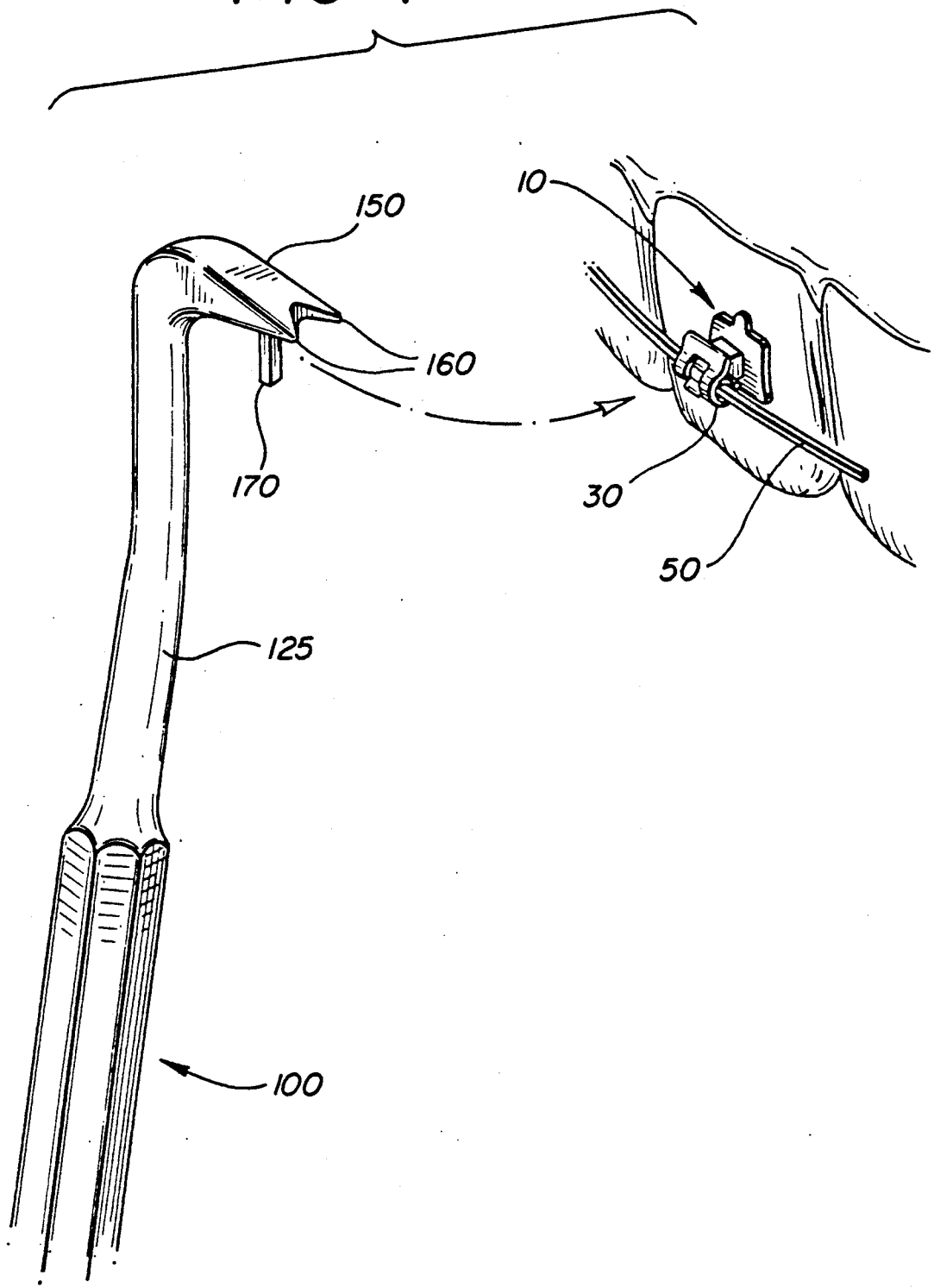
FIG. 1 is a perspective view of a dental bracket containing archwire and used in connection with the present invention.
Figure 2:
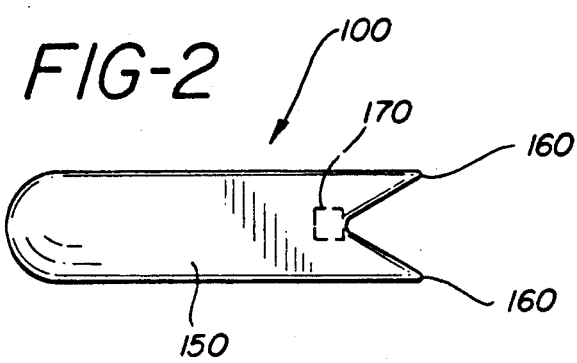
FIG. 2 is an top elevation view of a dental bracket instrument of the present invention.
Figure 3:
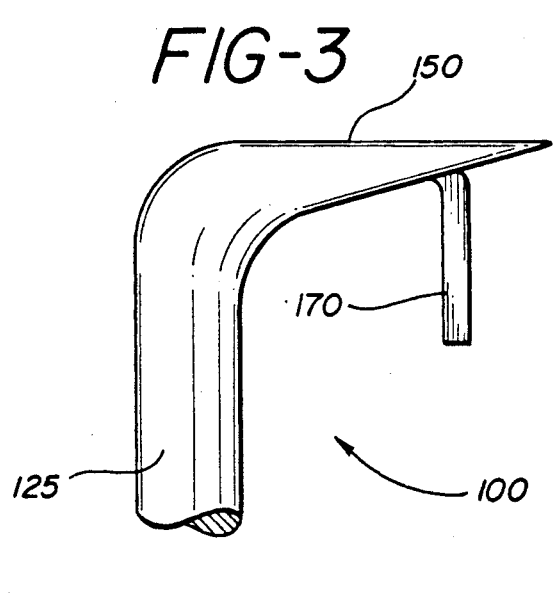
FIG. 3 is a side plan view of a dental bracket instrument of the present invention.
Figure 4:
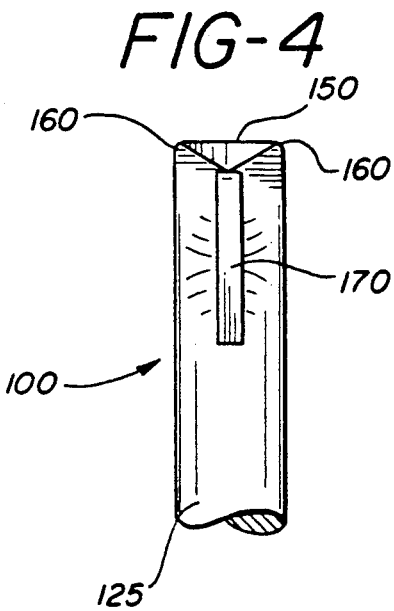
FIG. 4 is a front plan view of a dental bracket instrument of the present invention.
Figure 5:
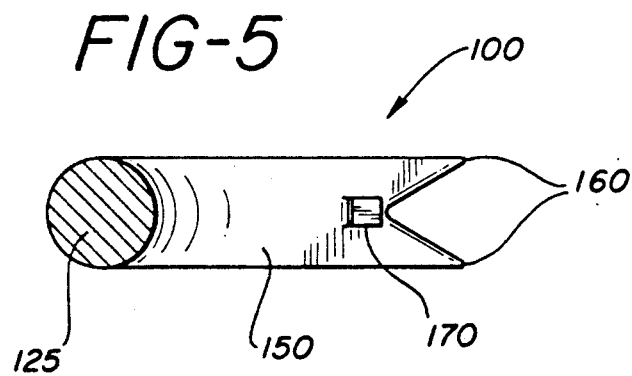
FIG. 5 is a bottom view of a dental bracket instrument of the present invention.
Figure 6:
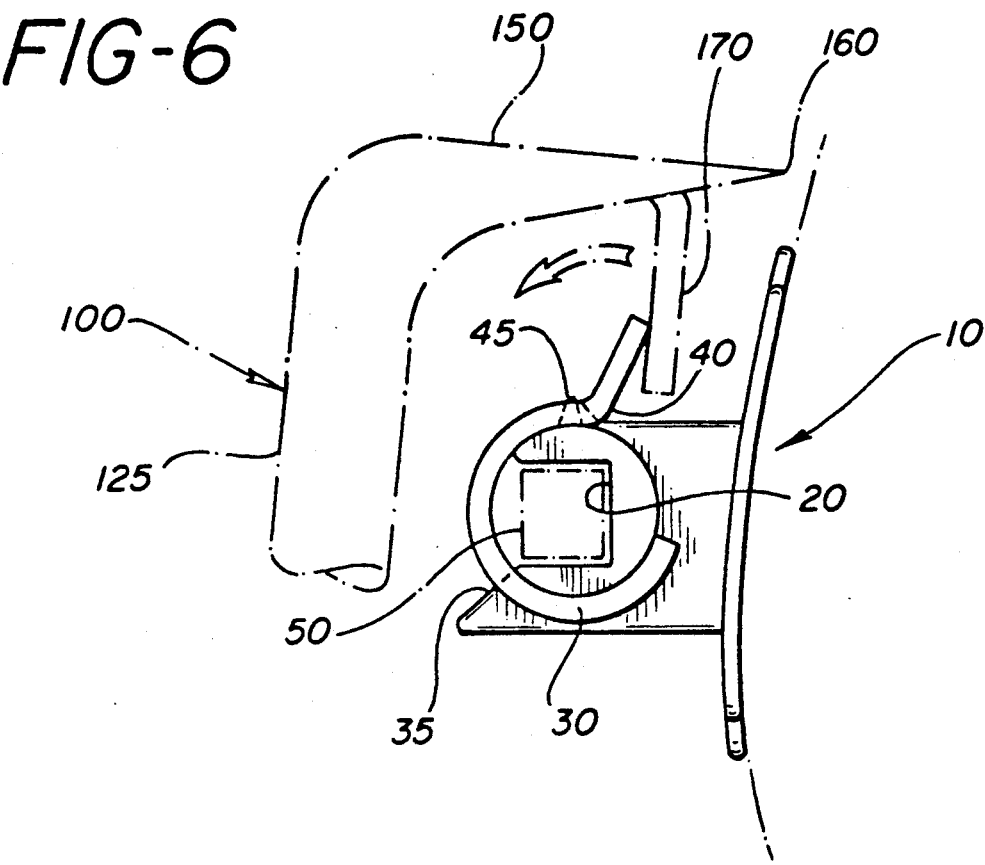
FIG. 6 is a side view of a closed bracket with the present invention shown in phantom.
Figure 7:
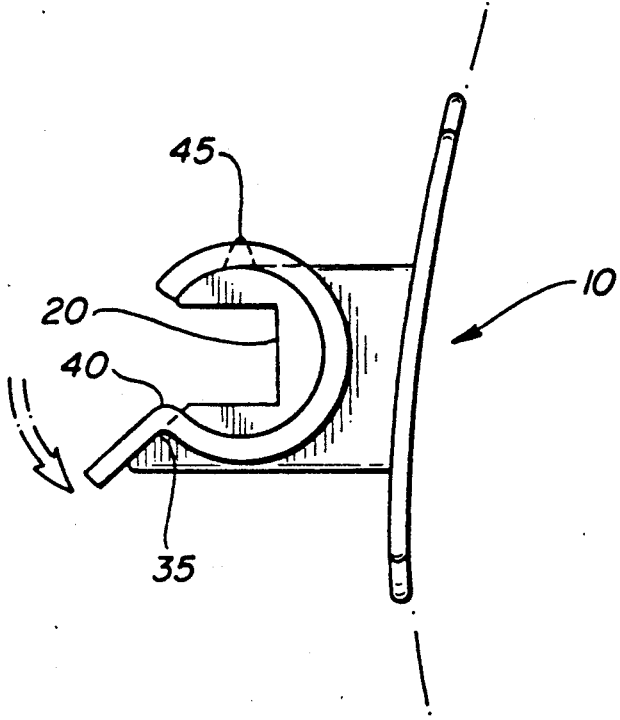
FIG. 7 is a side view of an open dental bracket.

As seen in FIGS. 1, 6 and 7, dental bracket 10 contains archwire slot 20 and rotating cover 30. This rotating cover 30 rotates about bracket 10 at opening 35 and allows clasp 40 to close over latch 45 on the dental bracket 10. In this way, the rotatable cover 30, when closed over archwire slot 20, retains archwire 50 which is either round or square within the slot 20 after emplacement on the bracket. One of the benefits behind creating cover 30 is the ability to remove and to replace any damaged or frayed archwire, or to increase tension on the archwire after emplacement into the mouth.

As better seen in FIGS. 1, 2, 3, 4 and 5, the instrument 100 of the invention contains a shaft or tube 125. This elongated tube 125 fits comfortably on the hand and allows the user to project the tube 125 into the mouth toward the dental brackets 10. At the end of tube 125 is a tapered flat surface 150 which projects at right angles to the shaft 125. Contained on surface 150 are projections 160 useful in probing during examination and to rotate the instrument about the archwire 50. In creating such a perpendicular tapered surface 150, the user is able to examine bracket placement and archwire strength.

Projecting at right angles from surface 150 about midway along said surface point 150 is bracket pusher or key 170. Key 170 may be placed behind clasp 40 on cover 30 and therefore pull cover 30 off of clasp 40 at latch 45. When this is done, the user is able to open hinged dental bracket 10 at opening 35 by using key 170 to rotate cover 30 on the bracket. Simultaneously, projections 160 rotate about the archwire 50.

As may be seen in FIG. 6, this arrangement works more conveniently and readily than tweezers, as the user is able to approach the dental bracket 10 from virtually any angle. If the user chooses, the bracket 10 may be opened so that key 170 is placed perpendicularly to bracket 10 and tool 100 is displacedly pulled toward the user. Alternately, key 170 may be placed within the groove behind clasp 40, and tool 100 rotated to open the cover 30. In this second manner, key 170 presents a large surface area along cover 30 to open cover 30 off latch 45.

In this way, the hands stay removed from the dental bracket and therefore are able to more readily open and close the dental bracket. In brackets farther into the mouth, there is no clumsy motion typical of tweezers. Rather, with the projecting tapered surface 150 and key 170, the user approaches the dental bracket comfortably and can open and close the mouth without difficulty.

It is to be understood that the invention which forms a dental bracket instrument, is disclosed by the following claims and their equivalents.

What is claimed is:

1. An orthodontic system comprising a dental bracket having an archwire slot and a cover which encloses said slot, said cover having a generally flat surface along said bracket and rotating about said slot into said bracket, said cover creating a groove behind said cover on said bracket, and an instrument comprising a key which fits within said groove, said key extending at a perpendicular angle to a planar surface having a distal end and a proximal end, said planar surface containing a pair of pointed projections at said distal end.

2. The system of claim 1 further containing a tube connected to its proximal end, said tube parallel to said key.

3. The system of claim 1 wherein said key has a rectangular cross-section.

4. The system of claim 1 wherein said key extends from said planar surface midway along said planar surface.

* * * * *